United States Patent [19]

Benardella

[11] Patent Number: Plant 6,517

[45] Date of Patent: Jan. 10, 1989

[54] ROSE PLANT NAMED BENALAY

[75] Inventor: Frank A. Benardella, Old Tappen, N.J.

[73] Assignee: Nor'East Miniature Roses, Inc., Rowley, Mass.

[21] Appl. No.: 30,429

[22] Filed: Mar. 26, 1987

[51] Int. Cl.[4] ..... A01H 5/00

[52] U.S. Cl. ..... Plt./7

[58] Field of Search ..... Plt. 7

*Primary Examiner*—Robert E. Bagwill

*Attorney, Agent, or Firm*—Vincent G. Gioia

[57] ABSTRACT

A new purple and near white bicolored miniature rose variety.

1 Drawing Sheet

The present invention relates to a new and distinct variety of rose plant of the miniature rose class, which was originated by my crossing as seed parent the rose known as "Rise 'N Shine" (U.S. Plant Pat. No. 4,231) and as pollen parent the rose known as "Laguna". The denomination of this new rose is "Benalav".

Among the novel characteristics possessed by this new variety which distinguish it from its parents and all other varieties of which I am aware are its unusual purple or lavender and near white bicolored flowers which are long lasting on the plant and after cutting. Asexual reproduction by budding of the new variety as performed in Essex County, Mass. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "11D" is plate 11D of The Royal Horticultural Society Colour Chart.

Parentage: Seedling.

*Seed parent.*—"Rise 'N Shine".

*Pollen parent.*—"Laguna".

Class: Miniature.

The following observations are made of specimens grown outdoors in Essex County, Mass., during the month of September.

FLOWER

Blooming habit: Recurrent.

A. Bud:

(1) *Size.*—Large.

(2) *Form.*—Long pointed.

(3) *Color.*—After sepals fall bud color is Empire yellow near 11D at petal base becoming near Fuchsia purple 67B to 67D with tonality deepest at petal edge. Yellow and purple coloring blend into each other until purple color predominates.

(4) *Sepals.*—Relatively smooth, longer than bud.

(5) *Peduncle.*—Length — about 1¼ inches. Aspect — straight. Strength — erect. Color — near 144B.

B. Bloom:

(1) *Size.*—Average size when fully expanded — about 1¾ inches.

(2) *Borne.*—Usually singly, one to a stem.

(3) *Form.*—High centered. Petals roll under.

(4) *Petalage.*—Number of petals under normal conditions — about 32 to 35.

(5) *Color.*—As petals unfurl, top surface of petals are a blend of lavender pink or purple coloring near 73A through 73D and near white. Color mixing of purple and near white is sometimes blending and washing and sometimes more distinct but generally with irregular transition zones. Petal undersurface remains generally paler toned with slight lavender pink veining and washing. As flowers open and age, color becomes lighter toned but with darker color at petal edges.

C. Petals:

(1) *Texture.*—Thick.

(2) *Appearance.*—Inside velvety and outside satiny.

(3) *Form.*—Broad, fan shaped.

(4) *Arrangement.*—Regularly arranged.

(5) *Petaloids in center.*—Few.

(6) *Persistence.*—Drop off cleanly.

(7) *Fragrance.*—Slight.

(8) *Lasting quality.*—Very long lasting quality on plant and as cut flower.

REPRODUCTIVE ORGANS

A. Stamens, filaments and anthers:

*Arrangement and color.*—Regularly arranged around styles.

B. Pollen:

*Color.*—Near 16A.

C. Styles: Even, medium length.

D. Stigmas:

*Color.*—Near 156C.

E. Hips: None observed.

PLANT

A. Form: Upright.

B. Growth: Very vigorous, uniform branching.

*Height attained.*—About 15 to 20 inches.

C. Foliage: Compound 5 to 7 leaflets.

(1) *Size.*—Medium.

(2) *Quantity.*—Abundant.

(3) *Color.*—New foliage: Upper side — near 187B. Under side — near 187C. Old foliage: Upper side — near 137A. Under side — near to 138B.

(4) *Shape.*—Oval, pointed.

(5) *Texture.*—Upper side is semiglossy; under side is matte.

(6) *Edge.*—Serrate.

(7) *Serration.*—Ordinary.

(8) *Leaf stem.*—Color — near to 191A. Under side — near 144B.

(9) *Stipules.*—Medium, slightly bearded.

(10) *Resistance to disease.*—Blackspot — Average. Mildew — Average. Rust — Average.

D. Wood:

(1) *New wood.*—Color — near 137D. Bark — smooth.

(2) *Old wood.*—Color — near 143A. Bark — smooth.

E. Thorns:

(1) *Thorns.*—Quantity (main stalk) — few. On laterals from stalk — none. Form — short, straight pointed. Length — short. Color — near 185C. Position — irregular.

(2) *Prickles.*—None.

F. Winter hardiness: Needs protection in severe climates.

I claim:

1. A new and distinct variety of rose plant of the miniature rose class, substantially as shown and described, characterized particularly by purple and near white bicolored flowers of good form which are long lasting on the plant and after cutting.

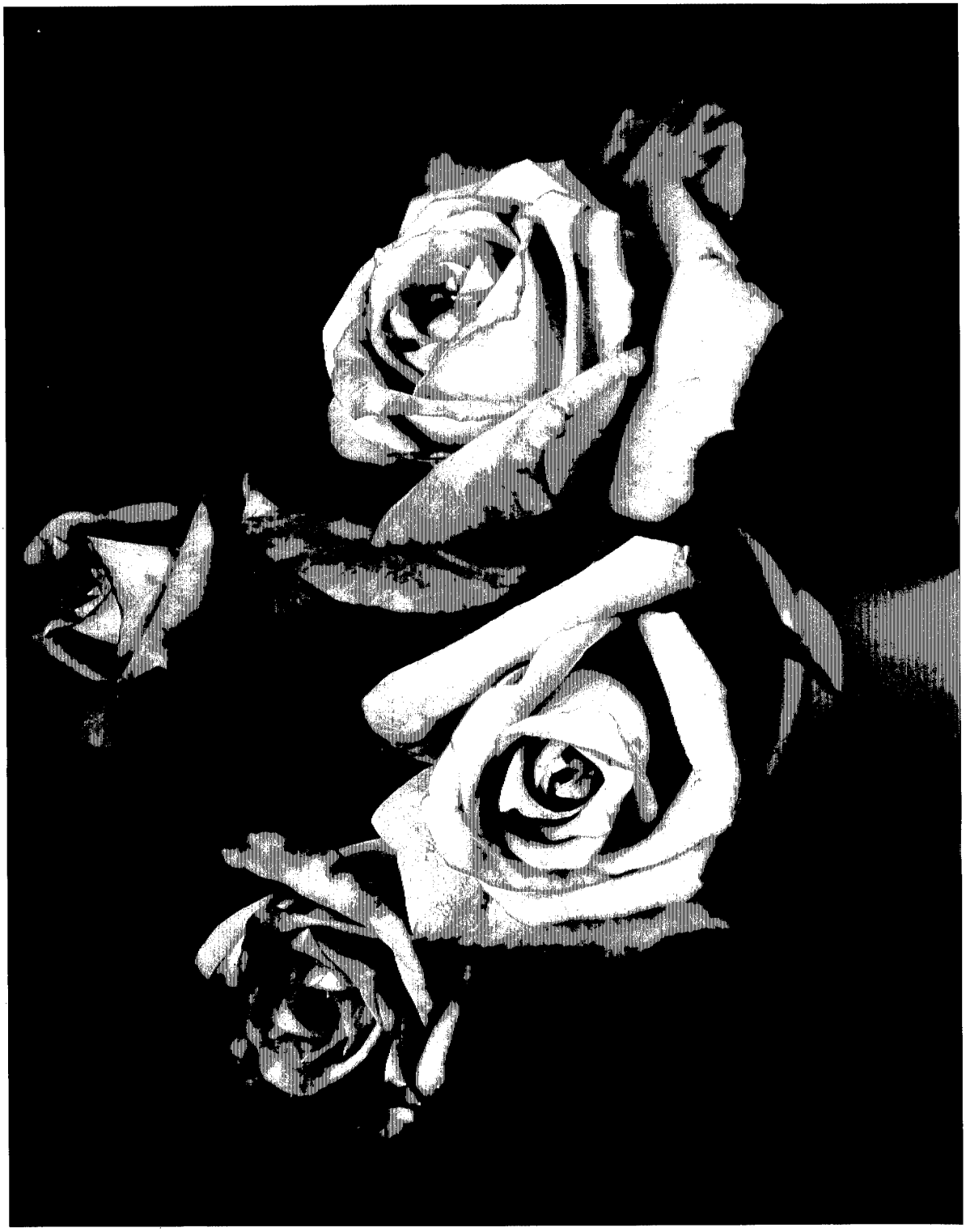

* * * * *